United States Patent
Jiang et al.

(10) Patent No.: US 9,909,966 B2
(45) Date of Patent: Mar. 6, 2018

(54) SHEAR TEST DEVICE AND TEST METHOD OF ROCK MASS DISCONTINUITIES UNDER CONSTANT NORMAL STIFFNESS CONDITION

(71) Applicant: Shandong University of Science and Technology, Qingdao, Shandong Province (CN)

(72) Inventors: Yujing Jiang, Qingdao (CN); Xuezhen Wu, Qingdao (CN); Gang Wang, Qingdao (CN)

(73) Assignee: Shandong University of Science and Technology, Qingdao (CN)

( * ) Notice: Subject to any disclaimer, the term of this patent is extended or adjusted under 35 U.S.C. 154(b) by 0 days.

(21) Appl. No.: 15/658,334

(22) Filed: Jul. 24, 2017

(65) Prior Publication Data

US 2018/0031457 A1 Feb. 1, 2018

(30) Foreign Application Priority Data

Jul. 26, 2016 (CN) .......................... 2016 1 0591608

(51) Int. Cl.
*G01N 3/24* (2006.01)
*G01N 3/02* (2006.01)
*G01N 33/24* (2006.01)

(52) U.S. Cl.
CPC .................. *G01N 3/24* (2013.01); *G01N 3/02* (2013.01); *G01N 33/24* (2013.01)

(58) Field of Classification Search
CPC ............. G01N 3/24; G01N 3/02; G01N 33/24

(Continued)

(56) References Cited

U.S. PATENT DOCUMENTS

2017/0284911 A1* 10/2017 Ni et al. ................... G01N 3/24

FOREIGN PATENT DOCUMENTS

CN 102253183 A 11/2011
CN 103792133 A 5/2014

(Continued)

OTHER PUBLICATIONS

Authors: Vincenzo Fioravante, Vito Nicola Ghionna, Sergio Pedroni, Daniela Forcino; Title: A constant normal stiffness direct shear box for soil-solid interface tests; Date: Yr. 1999; Publisher: Rivista Italiana Di Geotecnica; pp. 7-22.*

(Continued)

*Primary Examiner* — Lisa Caputo
*Assistant Examiner* — Roger Hernandez-Prewitt
(74) *Attorney, Agent, or Firm* — Loza & Loza, LLP; Michael Fedrick

(57) ABSTRACT

The present invention relates to a shear test device and test method of rock mass discontinuities under constant normal stiffness condition. The device includes: a base used for placing a test piece; a loading framework fixedly connected with the base; a shear loading system used for applying a shear force to the test piece; a normal loading system used for applying a normal pressure to the test piece; a normal displacement monitoring system used for measuring the magnitude of normal displacement of the test piece in real time; and a computer control system used for receiving the data of the normal displacement of the test piece in real time, and constantly adjusting the normal pressure applied by the normal loading system to the test piece according to the principle that the normal stiffness of the test piece is unchanged.

12 Claims, 5 Drawing Sheets

(58) Field of Classification Search
USPC .......................................... 73/784, 789, 841
See application file for complete search history.

(56) References Cited

FOREIGN PATENT DOCUMENTS

| | | |
|---|---|---|
| CN | 104749055 A | 7/2015 |
| CN | 105675409 A | 6/2016 |
| JP | 2002162326 A | 6/2002 |

OTHER PUBLICATIONS

Authors: Lean Hock Ooi and John P. Carter; Title: A Constant Normal Stiffness Direct Shear Device for Static and Cyclic Loading; Date: Mar. 1987; Publisher: Geotechnical Testing Journal, GTJODJ, vol. 10, No. 1; pp. 3-12.*

Authors: Heinz Konietzky, Thomas Fruhwirt and Hartmut Luge; Title: A New Large Dynamic Rockmechanical Direct Shear Box Device; Date: Jan. 5, 2012; Publication: Rock Mech Rock Eng (2012) 45; Publisher: Springer-Verlag; pp. 427-432.*

Chinese Patent Appl. No. 201610591608.5. Office Action dated Dec. 6, 2016, with partial English translation, total pp. 9.

Chinese Patent Appl. No. 201610591608.5. Search Report dated Oct. 10, 2016, with partial English ttranslation, total pp. 14.

* cited by examiner

SHEAR TEST DEVICE AND TEST METHOD OF ROCK MASS DISCONTINUITIES UNDER CONSTANT NORMAL STIFFNESS CONDITION

CROSS-REFERENCE TO RELATED APPLICATIONS

This application claims the benefit of priority under 35 U.S.C. § 119 from Chinese Patent Application No. 201610591608.5, filed Jul. 26, 2016. The disclosure of the foregoing application is incorporated herein by reference in its entirety.

FIELD OF THE INVENTION

The present invention relates to the technical field of underground engineering, and in particular to a shear test device and test method of rock mass discontinuities under constant normal stiffness.

BACKGROUND OF THE INVENTION

With the improvement of the level of modernization of the national economy and the increase of urban population, the contradiction between land occupation caused by residence and all kinds of activities of the human is increasingly intensified. From a macro point of view, the problems of human living spaces caused by the increase in population, the growth of living needs, the increasing deterioration of lands and other natural conditions and the gradual depletion of resources have reached to the extent of a crisis. In this case, the development and comprehensive utilization of underground space resources provide natural resources with huge potentials for the expansion of human living spaces.

However, in the development and utilization of underground space, it is necessary to classify the surrounding rock types of engineering and support excavated rock masses according to the relevant classification conditions of the surrounding rocks. If the excavated rock masses are not appropriately supported, engineering accidents such as the collapse of the surrounding rocks will happen, resulting in huge economic losses and also bringing threats to the life safety of construction workers. Therefore, the accuracy of the classification of the surrounding rocks and the feasibility of the geotechnical engineering support design are of great significance to ensure the construction safety of the engineering and save the economic cost of the engineering. In the process of classification of the surrounding rocks and the support design, the accurate selection of shear parameters of the rock masses plays an important role.

In the underground engineering, the rock mass will generate a dilatancy phenomenon in a shear process of discontinuities, and this dilatancy will be constrained due to the presence of the surrounding rock masses. The so-called discontinuities can also be referred to as a structural surface, including joints, cracks, faults and other conditions. As the discontinuity is rough and uneven, with the increase of the shear displacement and the continuous change of the dilatancy degree, the normal load of the surrounding rock masses on the discontinuity will also change continuously. In the process, only the stiffness of the surrounding rock masses remains constant.

The existing shear test machines can only achieve a constant load boundary, and this boundary condition can only simulate engineering conditions in which normal loads acting on discontinuities are unchanged, such as unsupported slopes. Both the rock mass in the underground engineering and the rock mass under anchoring conditions are under the boundary condition of constant normal stiffness, therefore the constant load boundary condition is not suitable for such engineering conditions anymore. The existing shear test machine cannot well simulate such engineering conditions.

In addition, existing shear test devices only consider the normal stress state, and cannot apply the required shear load under the condition of simulating the primary rock stress of the rock mass.

The above shortcomings of existing test shear instruments will cause the distortion of a simulation environment, resulting in greater difference between the obtained mechanical parameters and the actual situation, and even resulting in wrong determination of the classification of the surrounding rocks, misleading the reasonable selection of the excavation method and the support design, causing serious hidden troubles to construction safety or causing unnecessary waste of engineering economic costs.

SUMMARY OF THE INVENTION

The objective of the present invention is to overcome the shortcomings of the prior art and provide a shear test device and test method of rock mass discontinuities under constant normal stiffness, which can keep a test piece in a stress state similar to an engineering site and test shear mechanical parameters of the rock mass discontinuity under a constant normal stiffness boundary condition.

In order to achieve the above objective, the present invention adopts the following technical solutions:

A shear test device of rock mass discontinuities under constant normal stiffness includes:

a base used for placing a test piece;

a loading framework fixedly connected with the base;

a shear loading system 52 arranged on the base and used for applying a shear force to the test piece;

a normal loading system 52 fixedly connected with the top end of the loading framework and used for applying a normal pressure to the test piece;

a normal displacement monitoring system 58 used for measuring the magnitude of normal displacement of the test piece in real time; and a computer control system 56 connected with the normal loading system 54 and the normal displacement monitoring system 58 and used for receiving the data of the normal displacement of the test piece in real time, and constantly adjusting the normal pressure applied by the normal loading system 54 to the test piece according to the principle that the normal stiffness of the test piece is unchanged, namely the formula $\sigma = \sigma_0 + \Delta d * K$, in order to realize constant normal stiffness in a rock mass shear test process; and in the formula, $\sigma$ represents normal stress needing to be applied to the test piece at a certain moment, $\sigma_0$ represents an initial confining pressure of the test piece, $\Delta d$ represents the accumulated normal displacement of the test piece at the moment, K represents the normal stiffness of the test piece, and K is a constant value.

The control system adjusts the magnitude of the normal pressure applied to the test piece at any time by using the real-time feedback of the normal displacement by the normal displacement monitoring system, and thus the technical solution is advanced. The technical limitation that the traditional test machine can only achieve a constant load boundary is broken through, accordingly the continuous change of the normal load of the rock mass on the discontinuity and the constant stiffness of the surrounding rock mass can be simulated according to the real conditions of the surrounding rock in actual engineering, and the shear test of the rock mass discontinuity under the constant normal stiffness boundary condition is realized. The rock shear mechanical parameters obtained by the shear test device of constant normal stiffness better satisfy the actual conditions, so that the determination of the classification of the surrounding rocks and the selection of the excavation method and the support design are more scientific and accurate, and it is of great significance for the reasonable control on engineering construction safety and economic cost.

The shear test device of rock mass discontinuities under constant normal stiffness further includes a horizontal loading system used for applying a horizontal pressure vertical to the shear direction to the test piece.

In the engineering site, the rock mass is subjected to a horizontal shear force parallel to the shear direction and a horizontal pressure vertical to the shear direction in the horizontal direction. Ideal test equipment should firstly allow the test piece to meet the stress conditions of the normal direction and two horizontal directions of the engineering site, and then apply the required shear load. The traditional test machine ignores the simulation of the horizontal pressure, resulting in distortion of the simulation environment. By adoption of the horizontal loading system, the simulation of the horizontal pressure can be carried out before the shear test, so that the simulation environment of the test is consistent with the true stress environment of the rock mass in the surrounding rock, and the accuracy of the test result is ensured.

A test piece fixing member used for fixing the test piece is arranged on the base, the fixing member is composed of an upper fixing part and a lower fixing part, which are separate from each other, and the interior of the fixing member forms a space for accommodating the test piece; the horizontal loading system includes a hydraulic bag, and the hydraulic bag is arranged on the inner side of a side wall of the fixing member and is connected with a servo oil source; and the servo oil source is connected with the computer control system.

The computer control system controls the servo oil source to pressurize the hydraulic bag 25 to expand the hydraulic bag 25, and applies the horizontal pressure to the test piece 20 by means of the tight extrusion between the hydraulic bag 25 and the side wall 24.

As the horizontal pressure is applied by the hydraulic bag 25 rather than a traditional cylinder, the structure of the test machine is more compact, the space is reasonably used, the layout is reasonable, the occupation area of the instrument is reduced, and the cost is low. The hydraulic bag 25 is pressurized under the control of the computer control system, thereby being convenient and accurate.

The normal loading system includes two loading cylinders arranged in parallel and used for applying the normal pressure to the test piece. As the two loading cylinders parallel to each other are arranged, the normal stress of the test piece can be more uniform.

The shear loading system includes a first shear loading component and a second shear loading component used for applying the shear force to the test piece and arranged on both sides of the test piece.

The first shear loading component and the second shear loading component are arranged to be opposite to each other on both sides of the test piece along the shear direction, the first shear loading component includes a first shear loading cylinder located at the lower side and a third shear loading cylinder located at the upper side, and the second shear loading component includes a second shear loading cylinder located at the lower side and a fourth shear loading cylinder located at the upper side.

The shear loading system is connected with the computer control system, and each shear loading cylinder is independently controlled by the computer control system.

The stress condition of the rock mass in the surrounding rock is very complicated, when the rock mass is subjected to a shear action on a structural surface, and the shear action is generated on the basis of the primary rock stress. The traditional shear test instrument is generally constructed in such a way that staggered loading members are arranged on both sides of the test piece, and the primary rock stress of the rock mass along the shear direction cannot be considered. The shear loading system is provided with four loading cylinders, each loading cylinder is independently controlled by the computer control system, thereby being convenient and flexible, the actual stress of the rock mass in the vicinity of the structural surface can be simulated according to the actual situation of the surrounding rock, the primary rock stress along the shear direction can be considered while the shear force is simulated, so that the shear simulation process better satisfies the stress condition of the surrounding rock in actual geology, and it is possible to realize the real simulation of the stress environment of the rock mass.

The shear loading system further includes a first cylinder body fixing part and a second cylinder body fixing part, wherein both the cylinder body of the first shear loading cylinder and the cylinder body of the third shear loading cylinder are fixed in the first cylinder body fixing part, and both the cylinder body of the second shear loading cylinder and the cylinder body of the fourth shear loading cylinder are fixed in the second cylinder body fixing part.

A first force transmission shaft and a second force transmission shaft arranged along the front-back direction are separately arranged on the first cylinder body fixing part and the second cylinder body fixing part, and the force transmission shafts extend to the outer sides of the front and back surfaces of the cylinder body fixing parts to form projections; and the projections of the first and second force transmission shafts are connected by force transmission rods. The first and second shear loading components provide counterforce through the force transmission shafts and the force transmission rods, the structure is simple, the cost is low and the space utilization rate is high.

Two force transmission rods are provided and are arranged on front and back sides of the first and second cylinder body fixing parts.

The shear loading system further includes a shear supporting device used for supporting the first or second shear loading component, wherein the shear supporting device is arranged along a movement extension direction of the first or second shear loading component, and the surface of the shear supporting device is parallel to the surface of the base.

Both of the first cylinder body fixing part and the second cylinder body fixing part are fixedly connected with the base.

A cushion plate in direct contact with the surface of the test piece is arranged on the end head of a piston rod of the first, second, third and/or fourth shear loading cylinder.

A ball plate is arranged between the test piece fixing member and the base, so that the friction force between the test piece fixing member and the base can be reduced, and the simulated stress of the rock mass is guaranteed to better satisfy the actual condition.

The shear test device of rock mass discontinuities under constant normal stiffness further includes a monitoring system, wherein the monitoring system includes the normal displacement monitoring system, and further includes one or more of a normal pressure monitoring system, a shear force monitoring system, a shear displacement monitoring system and a horizontal force monitoring system.

The normal displacement monitoring system includes a displacement meter used for measuring the magnitude of the normal displacement of the test piece, and a displacement data collector.

The normal pressure monitoring system includes a pressure sensor used for measuring the magnitude of the axial pressure of the test piece, and a normal pressure data collector.

The shear force monitoring system includes four pressure monitoring systems used for respectively monitoring corresponding pressures of the four shear loading cylinders. Pressure monitors are arranged on four different shear loading cylinders to conveniently monitor and adjust the numerical values of the corresponding primary rock stress and the shear force, thereby providing convenience for the real simulation of the stress environment of the rock mass.

The shear displacement monitoring system includes a plurality of displacement meters used for respectively measuring the displacement values of the loading cylinders in the first and second shear loading components, and a shear displacement data collector.

The horizontal force monitoring system includes a hydraulic sensor used for measuring the magnitude of the horizontal force vertical to the shear direction, and a horizontal force confining pressure data collector.

A shear test method of rock mass discontinuities under constant normal stiffness includes the following steps:

step 1: applying an original horizontal shear force, an original horizontal pressure and an original normal pressure for simulating the original stress conditions of rock mass in a surrounding rock to the test piece, wherein the method for applying the original horizontal shear force is as follows: the force application values of the first, second, third and fourth shear loading cylinders to the test piece are equal to the original shear force value of the surrounding rock; and step 2: keeping the pressures of the second and third shear loading cylinders unchanged, keeping the displacement of the fourth shear loading cylinder unchanged, controlling the first shear loading cylinder to move toward the test piece at a constant speed to apply the shear force, obtaining the data of normal displacement of the test piece in real time in the process, and constantly adjusting the normal pressure applied to the test piece according to the principle that the normal stiffness of the test piece is unchanged, in order to realize a constant normal stiffness condition in a rock mass shear test process.

The shear performance of the rock mass on the discontinuity will vary greatly due to different stress environments. By means of the four independent cylinders, the original stress condition of the rock mass can be simulated at the beginning of the test, and the stress environment of the surrounding rock can be simulated continuously when the shear force occurs. In the whole test process, the cylinder applying the shear force applies the shear force to test piece at a constant speed, thereby better satisfying the shear stress condition of the rock mass in the actual engineering; for the part adjacent to a direct stress area of the test piece, the magnitude of the stress is still the state of the primary rock stress, and thus the pressures of the second and third shear loading cylinders are kept unchanged; and the force application position of the fourth shear loading cylinder to the test piece and the direct stress area are on a diagonal line, and the displacement of the fourth shear loading cylinder is kept unchanged to provide the counterforce for the shear force. By means of the control on the above four cylinders, continuous simulation of the stress environment of the rock mass in the whole test process can be realized, the shear force stress process of the rock mass discontinuity can be truly simulated, the obtained mechanical parameters are more accurate, and the accurate judgment of the classification of the surrounding rocks and the accuracy of reasonable selection of the support design are greatly improved.

The horizontal shear force is parallel to the shear direction, the horizontal pressure is vertical to the shear direction, and the direction of the normal pressure is a vertical direction.

The shear force herein refers to an increment of the shear force that is continued to be applied to the test piece on the basis of the original horizontal shear force.

Further, in step 2, after the shear displacement of the test piece reaches a set value, the shear force is unloaded to make the test piece reach the level of the primary rock stress again, the pressures of the first and fourth shear loading cylinders are kept unchanged, the displacement of the third shear loading cylinder is kept unchanged, the second shear cylinder is controlled to move toward the test piece at a constant speed to apply a reverse shear force, and the reverse shear force is unloaded to accomplish a shear cycle when the shear displacement of the test piece reaches the set value; and in the process, the constant normal stiffness condition of the test piece is satisfied.

The operations in step 2 are repeated to realize multiple shear cycles.

Another shear test method of rock mass discontinuities under constant normal stiffness includes the following steps:

step 1: applying a horizontal shear force, a horizontal pressure and a normal pressure for simulating the original stress conditions of rock mass in a surrounding rock to the test piece, wherein the horizontal shear force is parallel to the shear direction, the horizontal pressure is vertical to the shear direction, and the direction of the normal pressure is the vertical direction; and step 2: further applying the horizontal shear force to the test piece, obtaining the data of normal displacement of the test piece in real time in the process, and constantly adjusting the normal pressure applied to the test piece according to the principle that the normal stiffness of the test piece is unchanged, in order to realize a constant normal stiffness condition in a rock mass shear test process.

The traditional test method cannot realize the test process of constant normal stiffness of the shear test piece. By obtaining the data of the normal displacement of the test piece and adjusting the normal pressure according to the principle that the normal stiffness is unchanged, the constant normal stiffness condition is realized through the cyclic feedback of the computer control system, the technical limitation that the traditional test machine can only achieve the constant load boundary is broken through, and the shear test process of the rock mass discontinuity under the constant normal stiffness condition is realized. The rock shear mechanical parameters obtained by the shear test method of constant normal stiffness better satisfy the actual conditions, so that the determination of the classification of the surrounding rocks and the selection of the excavation method and the support design are more scientific and accurate, and it is of great significance for the reasonable control on engineering construction safety and economic cost.

Further, in step 2, after the shear displacement of the test piece reaches the set value, the horizontal shear force is reversely loaded until the reverse shear displacement reaches the displacement set value, and one shear cycle of the shear test piece is accomplished.

The operations in step 2 are repeated to realize multiple shear cycles; and the constant normal stiffness condition of the test piece is satisfied in the whole process.

The horizontal shear force is reversely loaded to realize one shear cycle, multiple shear cycles are realized accordingly, and test reference is provided for the theoretical research on the shear mechanical parameters under the multiple shear cycles.

The present invention has the following beneficial effects:

The rock mass can reach the actual stress state of the engineering site at first, and the shear test of the rock mass discontinuity under the constant normal stiffness boundary condition is realized, cyclic shear tests can be carried out conveniently, and the physical and mechanical properties of the rock on the engineering site can be reproduced and tested more truly. The shear test of the rock mass discontinuity under the constant normal stiffness boundary condition has great significance for determining reasonable rock shear mechanical parameters so as to perform reasonable classification of the surrounding rocks, adopt a proper excavation method and carry out a reasonable support design.

The shear loading system and the horizontal loading system can simulate the primary rock stress of the rock mass in the horizontal direction, and the omnibearing stress condition of the shear test piece in three dimensions can be simulated in combination with the normal loading system, therefore the test result is more accurate.

Figure 1:
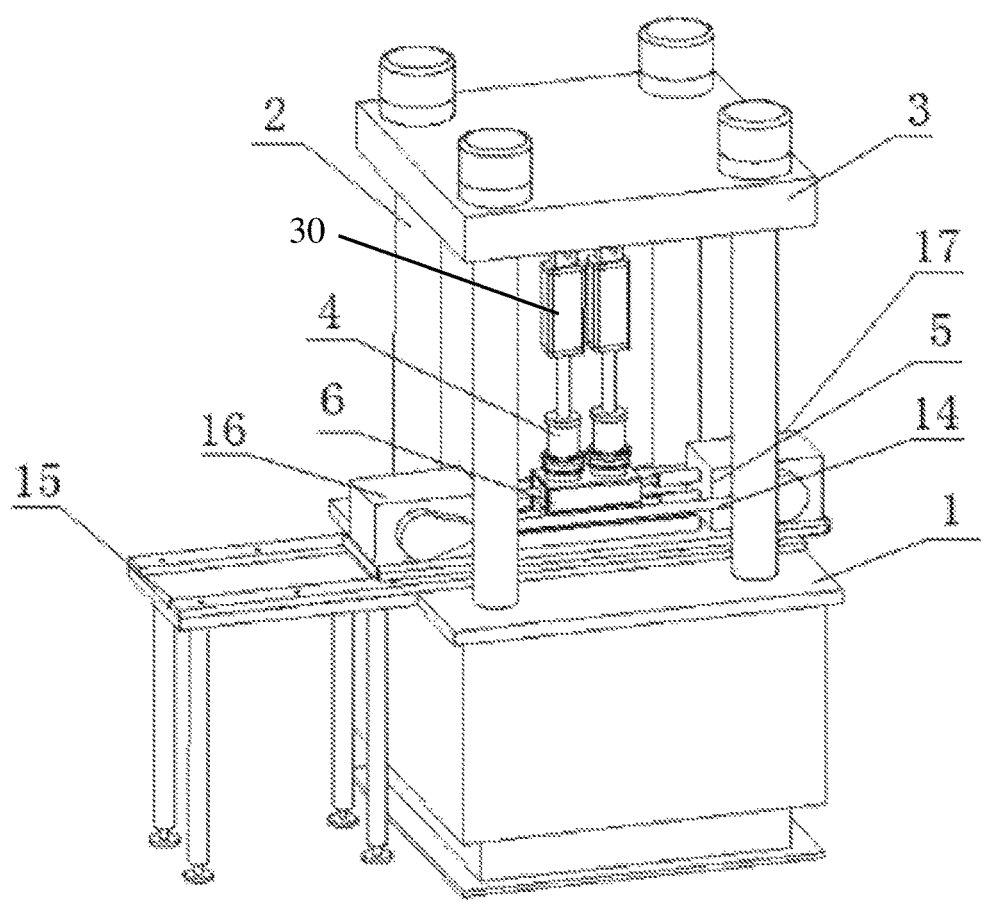
FIG. 1 is a structural schematic diagram of the present invention.

In the figures, the correspondence of reference numerals is shown as below: 1—base, 2—loading framework, 3—framework top plate, 4—normal hydraulic cylinder, 5—shear loading device, 6—test piece fixing member, 7—first shear loading cylinder, 8—second shear loading cylinder, 9—third shear loading cylinder, 10—fourth shear loading cylinder, 11—ball plate, 12—upper fixing part, 13—lower fixing part, 14—force transmission rod, 15—supporting device, 16—first cylinder body fixing part, 17—second cylinder body fixing part, 18—first force transmission shaft, and 19—second force transmission shaft.

DETAILED DESCRIPTION OF THE EMBODIMENTS

The present invention will be illustrated below in detail in combination with the drawings.

Embodiment 1

A shear test device of rock mass discontinuities under constant normal stiffness, as shown in FIG. 1, includes a base 1, a loading framework 2 and a normal loading system.

The normal loading system includes two normal hydraulic cylinders 4 vertically arranged in parallel, which are used for applying a normal pressure to the test piece, and a first servo oil source 30, which is used for driving the hydraulic cylinders 4 to apply the normal pressure to the rock test piece 40; and the hydraulic cylinders are fixed to a framework top plate 3.

Figure 2:
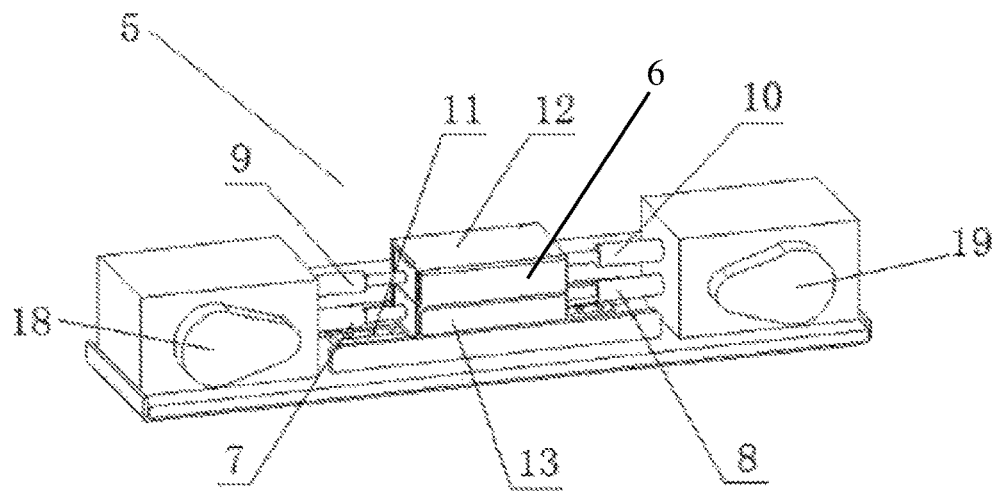
FIG. 2 is a structural schematic diagram of a shear loading system.

The shear test device of rock mass discontinuities under constant normal stiffness further includes a shear loading system, as shown in FIG. 2. A shear loading device 5 includes a supporting device 15, a shear loading framework, a first shear loading cylinder 7 and a cushion plate thereof, a second shear loading cylinder 8 and a cushion plate thereof, a third shear loading cylinder 9 and a cushion plate thereof, a fourth shear loading cylinder 10 and a cushion plate thereof, a second servo oil source and a ball plate 11, and is used for loading horizontal primary rock stress and a shear force in a shear direction for the test piece; and the ball plate is located below the U-shaped loading framework at the lower side and is used for reducing the friction force between a test piece fixing member 6 and the base 1.

The shear loading system further includes a first cylinder body fixing part 16 and a second cylinder body fixing part 17, wherein the cylinder body of the first shear loading cylinder 7 and the cylinder body of the third shear loading cylinder 9 are fixed in the first cylinder body fixing part 16, and the cylinder body of the second shear loading cylinder and the cylinder body of the fourth shear loading cylinder are fixed in the second cylinder body fixing part 17, and a force transmission shaft 14 used for providing a counterforce for the first and second shear loading components is arranged between the first cylinder body fixing part 16 and the second cylinder body fixing part 17.

A first force transmission shaft 18 and a second force transmission shaft 19 arranged are separately arranged on the first cylinder body fixing part and the second cylinder body fixing part along front-back direction thereof, and the force transmission shafts 18, 19 extend to the outer sides of the front and back surfaces of the cylinder body fixing parts 16, 17 to form projections; and the projections of the first force transmission shaft 18 and the second force transmission shaft 19 are connected by force transmission rods 14. The first and second shear loading components provide the counterforce through the force transmission shafts and the force transmission rods, the structure is simple, the cost is low and the space utilization rate is high.

Two force transmission rods 14 are provided and are arranged on front and back sides of the first and second cylinder body fixing parts.

The supporting device 15 is used for supporting the first shear cylinder 7 and the third shear cylinder 9, the shear supporting device 15 is arranged along a movement extension direction of the first shear cylinder 7 and the third shear cylinder 9, and the surface of the shear supporting device is parallel to the surface of the base.

Figure 3:
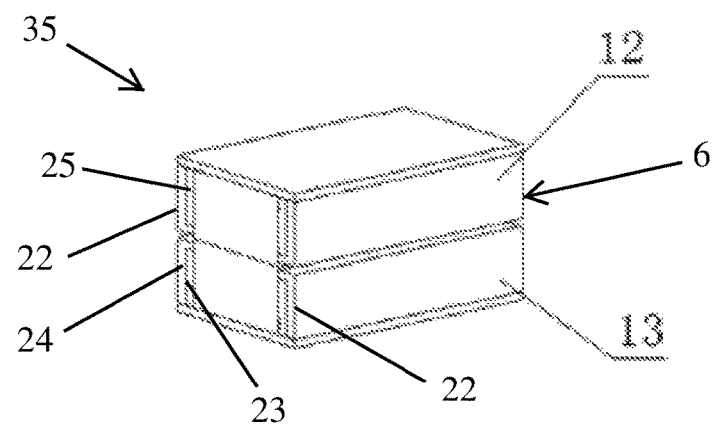
FIG. 3 is a structural schematic diagram of test piece fixing member.

The shear test device of rock mass discontinuities under constant normal stiffness further includes a horizontal loading system 35. The horizontal loading system 35 includes a third servo oil source, the test piece fixing member 6 and a hydraulic bag 25, which is used for applying the horizontal primary rock stress vertical to the shear direction to the test piece 40; the test piece fixing member 6 is a U-shaped loading framework 22, as shown in FIG. 3, two U-shaped loading frameworks 22 are provided in total, including an upper one and a lower one, the upper one is an upper fixing part 12 for keeping the U-shaped framework 22 upside down and the lower one is a lower fixing part 13 for holing the U-shaped framework upright. Two connected cavities are prefabricated on the inner sides of the U-shaped loading frameworks 22, and the two cavities constitute a space for accommodating the test piece 40 together. The hydraulic bag 25 is arranged on the inner side 23 of the side wall 24 of the U-shaped framework 22 and is driven by the third servo oil source 30 to apply the horizontal pressure to the test piece 40.

The shear test device of rock mass discontinuities under constant normal stiffness further includes a monitoring system. The monitoring system includes a normal pressure monitoring system, a normal displacement monitoring system, a shear force monitoring system, a shear displacement monitoring system, a shear direction horizontal force monitoring system and a monitoring system of horizontal force vertical to the shear direction.

The normal pressure monitoring system includes a pressure sensor and a normal pressure data collector, and is used for measuring the magnitude of the axial pressure of the test piece and transmitting it to a computer control system.

The normal displacement monitoring system includes a displacement meter and a displacement data collector, and is used for measuring the magnitude of the normal displacement of the test piece and transmitting it to the computer control system.

The shear force monitoring system includes four pressure sensors and a shear force data collector, wherein the four pressure sensors are respectively located between the first shear loading cylinder and the cushion plate thereof, between the second shear loading cylinder and the cushion plate thereof, between the third shear loading cylinder and the cushion plate thereof, and between the fourth shear loading cylinder and the cushion plate thereof, and the pressure sensors are used for measuring the magnitudes of the shear force and the horizontal primary rock stress in the shear direction of the rock test piece and transmitting them to the computer control system.

The shear displacement monitoring system includes displacement meters and a shear displacement data collector, and is used for respectively monitoring the magnitudes of the displacement of the three shear loading cylinders and transmitting them to the computer control system.

The monitoring system of horizontal force vertical to the shear direction includes a hydraulic sensor and a horizontal force confining pressure data collector.

Figure 4:
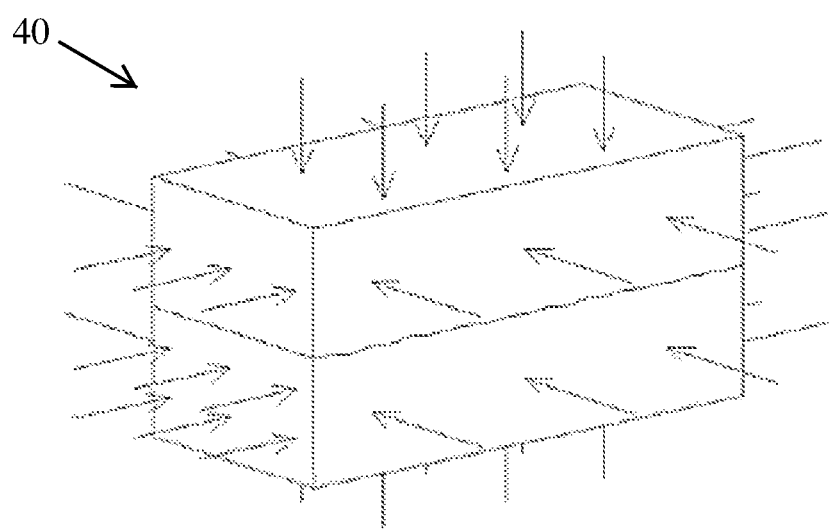
FIG. 4 is a stress diagram of a test piece.
Figure 5:
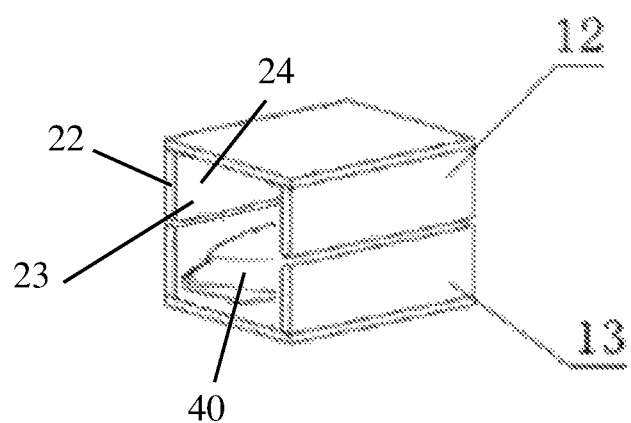
FIG. 5 is a partial cutaway view of the test piece fixing member of FIG. 3 with a test piece inside.
Figure 6:
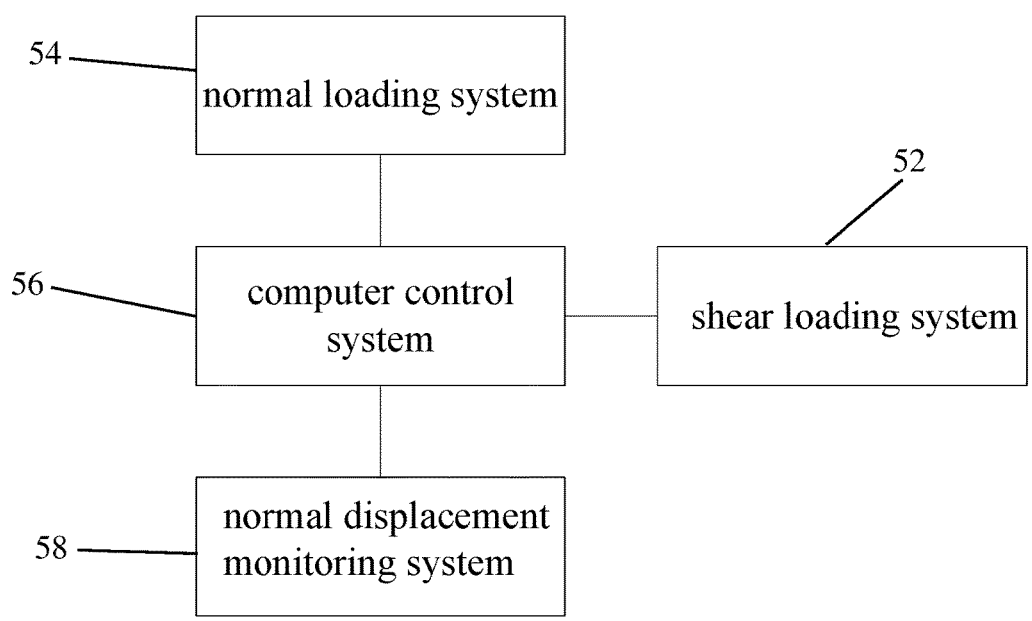
FIG. 6 is diagram showing the computer control system connected with the normal loading system, the normal displacement monitoring system and the shear loading system.

The computer control system includes a computer, control software, a data bus and a controller, and is used for providing a human-computer interaction interface, inputting experiment data, collecting monitoring data, controlling a loading process, realizing constant normal stiffness boundary control, and displaying and outputting an experiment result; the data bus is used for performing data format conversion and data transmission between the computer and the controller, and transmitting the monitoring data to the computer; the controller is used for receiving an instruction of the computer through the data bus, and controlling the loading systems to perform loading according to specific paths according to the instruction so as to realize the constant normal stiffness boundary control; the constant normal stiffness boundary control refers to: the rock test piece will generate a dilatancy phenomenon in a shear process, as the discontinuity is rough and uneven, with the continuous increase of the shear displacement, the dilatancy degree changes constantly, the normal pressure necessary for keeping the constant normal stiffness is calculated according to the monitored normal displacement of the test piece, and the magnitude of the normal pressure is corrected by the instruction sent by the computer control system in time so as to form a control cycle, and the control cycle is carried out continuously in the whole process of shear loading. The stress diagram of the test piece is as shown in FIG. 4.

A test method based on the shear test device of rock mass discontinuities under constant normal stiffness is as follows:

Firstly mounting the rock test piece in the U-shaped loading framework at first, and then mounting the rock test piece in a corresponding position of the test machine; applying the horizontal primary rock stress in the shear direction by the four cylinders of the shear loading system; applying the horizontal primary rock stress vertical to the shear direction by the horizontal loading system; applying a normal stress through the normal loading system; and controlling the first shear loading cylinder of the shear loading system to move at a constant speed to apply a rightward shear force to the test piece, and meanwhile keeping the pressures of the second shear loading cylinder and the third shear loading cylinder unchanged, and keeping the displacement of the fourth shear loading cylinder unchanged.

With the continuous increase of the shear force, the lower half part of the test piece gradually slides rightward, the normal displacement of the test piece is measured in real time in the process, the computer control system calculates the normal stress necessary for keeping the constant normal stiffness boundary according to the normal displacement, the computational formula is: $\sigma = \sigma_0 + \Delta d * K$, in the formula, $\sigma$ represents the normal stress needing to be applied to the test piece at a certain moment, $\sigma_0$ represents an initial confining pressure, $\Delta d$ represents the normal displacement of the rock test piece at a certain stage, and K represents the normal stiffness of the rock test piece; then the instruction is sent to constantly correct the magnitude of the normal stress until the experiment is ended; and the confining pressure, axial pressure, lateral deformation and axial deformation data of the rock test piece are recorded and output in the experiment process.

In the above test, after the shear displacement reaches the preset objective, cyclic shear tests can be carried out conveniently, and the specific method is as follows: unloading the shear force to make the test piece reach the level of the primary rock stress again; controlling the second shear loading cylinder of the shear loading system to move at a constant speed to apply a leftward shear force to the test piece, and meanwhile keeping the pressures of the first shear loading cylinder and the fourth shear loading cylinder unchanged, and keeping the displacement of the third shear loading cylinder unchanged; after the shear displacement reaches the preset objective, unloading the shear force to accomplish one shear cycle; and the above steps can be repeated according to demands to realize multiple shear cycles.

Embodiment 2

The shear loading system can also be replaced by an ordinary shear loading mechanism, for example, staggered loading components can be arranged on both sides of the test piece to realize the shear test of the test piece.

The horizontal loading system can be replaced by a horizontal hydraulic cylinder vertical to the shear direction to simulate the horizontal pressure of the test piece.

The foregoing description of the disclosed embodiments will enable those skilled in the art to implement or use the present invention. Various modifications to the embodiments will be apparent to those skilled in the art, and the general principles defined herein may be embodied in other embodiments without departing from the spirit or scope of the present invention. The parts not described in detail are the prior art and are not repeated redundantly herein. Accordingly, the present invention will not be limited to these embodiments shown herein, but needs to satisfy the widest scope consistent with the principles and features disclosed herein.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

The invention claimed is:

1. A shear test device for rock mass discontinuities under constant normal stiffness conditions, comprising:
    a base used for placing a test piece;
    a loading framework fixedly connected with the base;
    a shear loading system arranged on the base and used for applying a shear force to the test piece;
    a normal loading system fixedly connected with the top end of the loading framework and used for applying a normal pressure to the test piece;
    a normal displacement monitoring system used for measuring the magnitude of normal displacement of the test piece in real time; and
    a computer control system connected with the normal loading system and the normal displacement monitoring system and used for receiving the data of the normal displacement of the test piece in real time,
    wherein the computer control system is constantly adjusting the normal pressure applied by the normal loading system to the test piece according to the principle that the normal stiffness of the test piece is unchanged, the computer control system using the formula $\sigma=\sigma_0+\Delta d * K$ in order to realize constant normal stiffness in a rock mass shear test process, wherein in the formula $\sigma$ represents normal stress needed to be applied to the test piece at a certain moment, $\sigma_0$ represents an initial confining pressure of the test piece, $\Delta d$ represents the accumulated normal displacement of the test piece at the moment, $K$ represents the normal stiffness of the test piece, and $K$ is a constant value;
    wherein the shear loading system comprises a first shear loading component and a second shear loading component used for applying the shear force to the test piece and arranged on both sides of the test piece, the first shear loading component and the second shear loading component being arranged to be opposite to each other on both sides of the test piece along a shear direction, wherein the first shear loading component comprises a first shear loading cylinder located at the lower side and a third shear loading cylinder located at the upper side, and the second shear loading component comprises a second shear loading cylinder located at the lower side and a fourth shear loading cylinder located at the upper side; and
    wherein the shear loading system is connected with the computer control system, and the shear loading cylinders are independently controlled by the computer control system.

2. The shear test device of claim 1, wherein the normal loading system comprises two loading cylinders arranged in parallel and used for applying the normal pressure to the test piece.

3. A test method using the shear test device of claim 2, comprising the following steps:
    (1) applying an original horizontal shear force, an original horizontal pressure and an original normal pressure for simulating the original stress conditions of rock mass in a surrounding rock to the test piece, wherein the method for applying the original horizontal shear force is as follows: the force application values of the first, second, third and fourth shear loading cylinders to the test piece are equal to the original shear force value of the surrounding rock; and
    (2) keeping the pressures of the second and third shear loading cylinders unchanged, keeping the displacement of the fourth shear loading cylinder unchanged, controlling the first shear loading cylinder to move toward the test piece at a constant speed to apply the shear force, obtaining the data of normal displacement of the test piece in real time in the process, and constantly adjusting the normal pressure applied to the test piece according to the principle that the normal stiffness of the test piece is unchanged, in order to realize a constant normal stiffness condition in a rock mass shear test process.

4. The test method of claim 3, wherein in step (2), after the shear displacement of the test piece reaches a set value, unloading the shear force to make the test piece reach the level of the primary rock stress again, keeping the pressures of the first and fourth shear loading cylinders unchanged, keeping the displacement of the third shear loading cylinder unchanged, controlling the second shear cylinder to move toward the test piece at a constant speed to apply a reverse shear force, and when the shear displacement of the test piece reaches the set value, unloading the reverse shear force to accomplish a shear cycle; and in the process, the constant normal stiffness condition of the test piece is satisfied.

5. The shear test device of claim 1, wherein the shear test device further comprises a horizontal loading system used for applying a horizontal pressure vertical to the shear direction to the test piece.

6. The shear test device of claim 5, wherein a test piece fixing member used for fixing the test piece is arranged on the base, the fixing member being composed of an upper fixing part and a lower fixing part, which are separate from each other, and the interior of the fixing member forming a space for accommodating the test piece; wherein the horizontal loading system comprises a hydraulic bag, and the hydraulic bag is arranged on the inner side of a side wall of the fixing member and is connected with a servo oil source; and wherein the servo oil source is connected with the computer control system.

7. A test method using the shear test device of claim 6, comprising the following steps:
   (1) applying an original horizontal shear force, an original horizontal pressure and an original normal pressure for simulating the original stress conditions of rock mass in a surrounding rock to the test piece, wherein the method for applying the original horizontal shear force is as follows: the force application values of the first, second, third and fourth shear loading cylinders to the test piece are equal to the original shear force value of the surrounding rock; and
   (2) keeping the pressures of the second and third shear loading cylinders unchanged, keeping the displacement of the fourth shear loading cylinder unchanged, controlling the first shear loading cylinder to move toward the test piece at a constant speed to apply the shear force, obtaining the data of normal displacement of the test piece in real time in the process, and constantly adjusting the normal pressure applied to the test piece according to the principle that the normal stiffness of the test piece is unchanged, in order to realize a constant normal stiffness condition in a rock mass shear test process.

8. The test method of claim 7, wherein in step (2), after the shear displacement of the test piece reaches a set value, unloading the shear force to make the test piece reach the level of the primary rock stress again, keeping the pressures of the first and fourth shear loading cylinders unchanged, keeping the displacement of the third shear loading cylinder unchanged, controlling the second shear cylinder to move toward the test piece at a constant speed to apply a reverse shear force, and when the shear displacement of the test piece reaches the set value, unloading the reverse shear force to accomplish a shear cycle; and in the process, the constant normal stiffness condition of the test piece is satisfied.

9. A test method using the shear test device of claim 5, comprising the following steps:
   (1) applying an original horizontal shear force, an original horizontal pressure and an original normal pressure for simulating the original stress conditions of rock mass in a surrounding rock to the test piece, wherein the method for applying the original horizontal shear force is as follows: the force application values of the first, second, third and fourth shear loading cylinders to the test piece are equal to the original shear force value of the surrounding rock; and
   (2) keeping the pressures of the second and third shear loading cylinders unchanged, keeping the displacement of the fourth shear loading cylinder unchanged, controlling the first shear loading cylinder to move toward the test piece at a constant speed to apply the shear force, obtaining the data of normal displacement of the test piece in real time in the process, and constantly adjusting the normal pressure applied to the test piece according to the principle that the normal stiffness of the test piece is unchanged, in order to realize a constant normal stiffness condition in a rock mass shear test process.

10. The test method of claim 9, wherein in step (2), after the shear displacement of the test piece reaches a set value, unloading the shear force to make the test piece reach the level of the primary rock stress again, keeping the pressures of the first and fourth shear loading cylinders unchanged, keeping the displacement of the third shear loading cylinder unchanged, controlling the second shear cylinder to move toward the test piece at a constant speed to apply a reverse shear force, and when the shear displacement of the test piece reaches the set value, unloading the reverse shear force to accomplish a shear cycle; and in the process, the constant normal stiffness condition of the test piece is satisfied.

11. A test method using the shear test device of claim 1, comprising the following steps:
   (1) applying an original horizontal shear force, an original horizontal pressure and an original normal pressure for simulating the original stress conditions of rock mass in a surrounding rock to the test piece, wherein the method for applying the original horizontal shear force is as follows: the force application values of the first, second, third and fourth shear loading cylinders to the test piece are equal to the original shear force value of the surrounding rock; and
   (2) keeping the pressures of the second and third shear loading cylinders unchanged, keeping the displacement of the fourth shear loading cylinder unchanged, controlling the first shear loading cylinder to move toward the test piece at a constant speed to apply the shear force, obtaining the data of normal displacement of the test piece in real time in the process, and constantly adjusting the normal pressure applied to the test piece according to the principle that the normal stiffness of the test piece is unchanged, in order to realize a constant normal stiffness condition in a rock mass shear test process.

12. The test method of claim 11, wherein in step (2), after the shear displacement of the test piece reaches a set value, unloading the shear force to make the test piece reach the level of the primary rock stress again, keeping the pressures of the first and fourth shear loading cylinders unchanged, keeping the displacement of the third shear loading cylinder unchanged, controlling the second shear cylinder to move toward the test piece at a constant speed to apply a reverse shear force, and when the shear displacement of the test piece reaches the set value, unloading the reverse shear force to accomplish a shear cycle; and in the process, the constant normal stiffness condition of the test piece is satisfied.

* * * * *